(12) United States Patent  
Ahoniemi et al.

(10) Patent No.: US 8,853,108 B2  
(45) Date of Patent: Oct. 7, 2014

(54) NONWOVEN MATERIAL AND ABSORBING ARTICLE COMPRISING NONWOVEN MATERIAL

(75) Inventors: Hannu Ahoniemi, Landvetter (SE); Daniel Burman, Mölndal (SE); Mikael Strandqvist, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 1330 days.

(21) Appl. No.: 12/094,011

(22) PCT Filed: Dec. 7, 2005

(86) PCT No.: PCT/SE2005/001849  
§ 371 (c)(1),  
(2), (4) Date: May 16, 2008

(87) PCT Pub. No.: WO2007/067100  
PCT Pub. Date: Jun. 14, 2007

(65) Prior Publication Data  
US 2008/0300562 A1    Dec. 4, 2008

(51) Int. Cl.  
*B32B 5/06*  (2006.01)  
*B32B 3/30*  (2006.01)  
(Continued)

(52) U.S. Cl.  
CPC  *D04H 1/732* (2013.01); *B32B 5/08* (2013.01); *D10B 2403/011* (2013.01); *D10B 2403/033* (Continued)

(58) Field of Classification Search  
CPC .......... B32B 3/263; B32B 3/30; B32B 5/022; B32B 5/06; B32B 5/08; B32B 5/14; B32B 5/142; B32B 5/147; B32B 2262/04; B32B 2262/062; B32B 2262/067; B32B 2262/14; B32B 2307/738; D04H 1/005; D04H 1/42; D04H 1/425; D04H 1/4258; D04H 1/46; D04H 1/465; D04H 1/492; D04H 1/495; D10B 2403/01; D10B 2403/011; D10B 2403/0112; D10B 2403/033; D10B 2403/0331; D10B 2403/0333  
USPC ........... 442/408, 415; 428/156, 170, 171, 172  
See application file for complete search history.

(56) References Cited

U.S. PATENT DOCUMENTS 5,475,903 A    12/1995   Collins .......................... 28/104  
5,525,397 A    6/1996    Shizuno et al.  
(Continued)

FOREIGN PATENT DOCUMENTS

CA    841938    5/1970  
CN    1364448   8/2002  
(Continued)

OTHER PUBLICATIONS

Russian Decision on Grant (English Translation) issued in RU Application No. 2008127402/14(033592).  
(Continued)

*Primary Examiner* — Jenna Johnson  
(74) *Attorney, Agent, or Firm* — Drinker Biddle & Reath LLP

(57) ABSTRACT

The present invention relates to a nonwoven material intended for use in absorbent products produced by the hydroentangling of a substrate web comprising at least one layer of fibers selected from amongst synthetic fibers, regenerated fibers and natural fibers, wherein the nonwoven material (1) has a base level $h_0$ with protuberances (2, 3) on one side, wherein the protuberances (2, 3) form at least a first and a second surface structure respectively in the form of first (2) and second (3) protuberances from the base level $h_0$, wherein the first protuberances (2) have a height $h_1$ from the base level and the second protuberances (3) have a height $h_2$ from the base level $h_0$, where $h_2$ is higher than $h_1$, and each of the second protuberances (3) occupies an area of the surface of the base level at least 4 times greater than each of the first protuberances (2).  
The invention also relates to an absorbent product containing a nonwoven material in accordance with the above.

16 Claims, 8 Drawing Sheets

(51) Int. Cl.
*B32B 5/14* (2006.01)
*D04H 1/42* (2012.01)
*D04H 1/46* (2012.01)
*D04H 1/732* (2012.01)
*B32B 5/08* (2006.01)
*B32B 5/02* (2006.01)
*B32B 3/26* (2006.01)
*A61F 13/511* (2006.01)
*D04H 1/492* (2012.01)
*D04H 1/495* (2012.01)
*D04H 1/498* (2012.01)
*D04H 1/74* (2006.01)
*D04H 3/11* (2012.01)
*D04H 3/16* (2006.01)
*D04H 5/03* (2012.01)

(52) U.S. Cl.
CPC . (2013.01); *D10B 2403/0112* (2013.01); *B32B 5/145* (2013.01); *B32B 5/022* (2013.01); *D10B 2403/0333* (2013.01); *B32B 3/263* (2013.01); *D10B 2403/0331* (2013.01); *B32B 3/30* (2013.01); *D10B 2403/01* (2013.01); *A61F 13/511* (2013.01); *D04H 1/492* (2013.01); *D04H 1/495* (2013.01); *D04H 1/498* (2013.01); *D04H 1/74* (2013.01); *D04H 3/11* (2013.01); *D04H 3/16* (2013.01); *D04H 5/03* (2013.01)
USPC ......... 442/408; 442/415; 428/156; 428/170; 428/171; 428/172

(56) References Cited

U.S. PATENT DOCUMENTS

| | | | |
|---|---|---|---|
| 2002/0034914 A1* | 3/2002 | De Leon et al. | 442/384 |
| 2002/0052582 A1 | 5/2002 | Takai et al. | |
| 2003/0008108 A1 | 1/2003 | Shizuno et al. | |
| 2003/0114071 A1 | 6/2003 | Everhart et al. | |
| 2004/0121120 A1 | 6/2004 | Gray et al. | |
| 2006/0063456 A1* | 3/2006 | Carter | 442/327 |

FOREIGN PATENT DOCUMENTS

| | | |
|---|---|---|
| EP | 0 625 602 | 11/1994 |
| EP | 1 022 003 | 7/2000 |
| EP | 1 338 262 | 8/2003 |
| GB | 1088376 | 10/1967 |
| GB | 2 335 627 | 9/1999 |
| RU | 2195910 C2 | 10/2003 |
| WO | 98/07914 | 2/1998 |
| WO | 98/25560 | 6/1998 |
| WO | WO 01/41622 A2 | 6/2001 |
| WO | 02/04729 | 1/2002 |
| WO | 03/083197 | 10/2003 |
| WO | WO 2004/073479 A2 | 9/2004 |
| WO | 2007/067101 | 6/2007 |

OTHER PUBLICATIONS

International Search Report mailed Jul. 7, 2006 issued in PCT Application No. PCT/SE2005/001850.
European Search Report issued May 27, 2010, in EP Application No. EP 05 81 5805.
Chinese Office Action issued Jul. 7, 2010, from corresponding patent application No. CN 200580052254.7.
U.S. Office Action dated Feb. 28, 2014 that issued in U.S. Appl. No. 12/096,189 including Double Patenting Rejections on pp. 5 and 6.

* cited by examiner

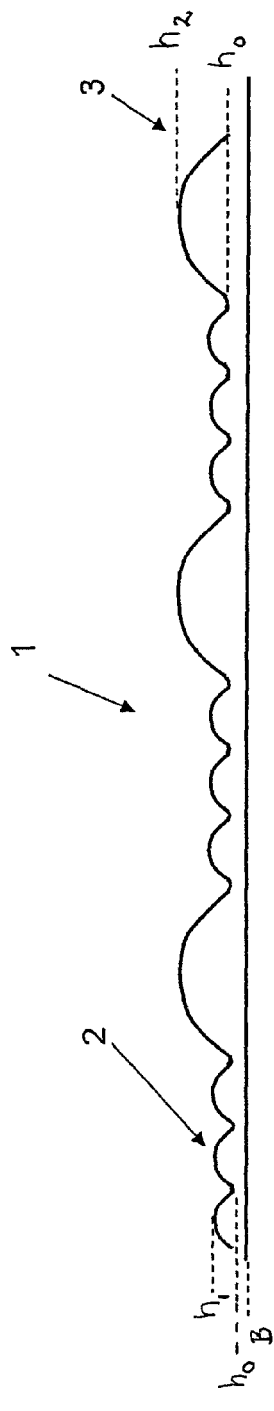
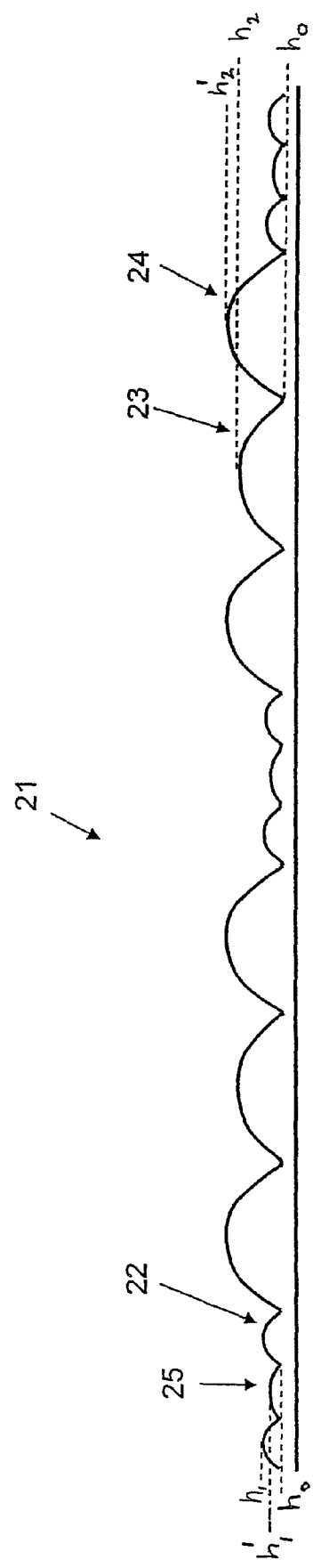
Fig. 1
Fig. 2

NONWOVEN MATERIAL AND ABSORBING ARTICLE COMPRISING NONWOVEN MATERIAL

RELATED APPLICATION DATA

This application is a §371 National Stage Application of PCT International Application No. PCT/SE2005/001849 filed Dec. 7, 2005.

TECHNICAL FIELD

The present invention relates to nonwoven material for use in absorbent products such as nappies, incontinence pads, sanitary towels and panty liners, etc., produced by hydroentangling and absorbent products containing such a nonwoven material.

BACKGROUND ART

Nonwoven material is often used as a surface layer in absorbent products such as nappies, incontinence pads, sanitary towels and panty liners, etc. It is customary in this case to apply an image or decoration to the nonwoven material by thermal embossing. In conjunction with embossing, the fibres are compressed by an embossing stamp, and the image is produced as a depression. The use of thermal embossing means that a number of fibres are caused to melt and are damaged, which reduces the softness of the surface, and this in turn impairs the strength characteristics of the material. The embossed image will also be situated beneath the base level of the nonwoven material, which leads to the image being less readily visible.

Images or decorations in nonwoven material can also be produced by hydroentangling. This can be done, for example, by means of hydroentangling against an image transfer surface. A substrate web of fibres is laid on the image transfer surface, wherein the substrate web is hydroentangled, that is to say it is sprayed with jets of liquid. The image transfer surface can be in the form of a wire gauze or a plate that exhibits depressions and/or projections. The nonwoven material receives its image or decoration against the wire gauze or the plate by being formed respectively against depressions and projections with the help of jets of liquid, and the nonwoven material receives an image or a decoration on both sides. A method of this kind is described in WO 02/04729. A nonwoven material produced in this way exhibits certain shortcomings with regard to its use in absorbent products. A poor contact surface with subjacent material may make it more difficult to glue in place, for example.

Another method for hydroentangling is described in WO 03/083197, where a nonwoven material with protuberances is produced. In this case, a plastic gauze is used as the carrier device for a web of fibres when it is hydroentangled.

EP 625 602 describes a nonwoven material that is used as a surface material in absorbent products. This nonwoven material has been hydroentangled so that it exhibits depressions on one side. The depressions retain liquid, which is not good for the distribution of liquid.

When nonwoven material is used as a surface layer in absorbent products, the ability to receive fluid is a significant characteristic. It is also important that the product does not lie too closely against the wearer's skin.

Layers of nonwoven material should also be easy to apply in absorbent products.

The intention of the invention is to solve the above problems and to improve nonwoven material.

SUMMARY OF INVENTION

The object of the present invention is to achieve a nonwoven material that possesses good liquid receiving characteristics, is comfortable for the wearer and has clear images in the form of decorative surface structures or decorations.

This is achieved by the invention with a nonwoven material intended for use in absorbent products produced by the hydroentangling of a substrate web comprising at least one layer of fibres selected from amongst synthetic fibres, regenerated fibres and natural fibres, wherein the nonwoven material has a base level with protuberances on one side. The protuberances form at least a first and a second surface structure respectively in the form of first and second protuberances from the base level, wherein the first protuberances have a height $h_1$ from the base level and the second protuberances have a height $h_2$ from the base level, where $h_2$ is higher than $h_1$, and each of the second protuberances occupies an area of the surface of the base level at least 4 times greater than each of the first protuberances. Also proposed is an absorbent product containing a nonwoven material in accordance with the above.

BRIEF DESCRIPTION OF DRAWINGS

The invention is now described below in greater detail with reference to the following Figures:

FIG. 1 shows a cross-sectional view of a nonwoven material in accordance with the invention.

FIG. 2 shows a cross-sectional view of a further nonwoven material in accordance with the invention.

DETAILED DESCRIPTION OF THE INVENTION

Figure 3:
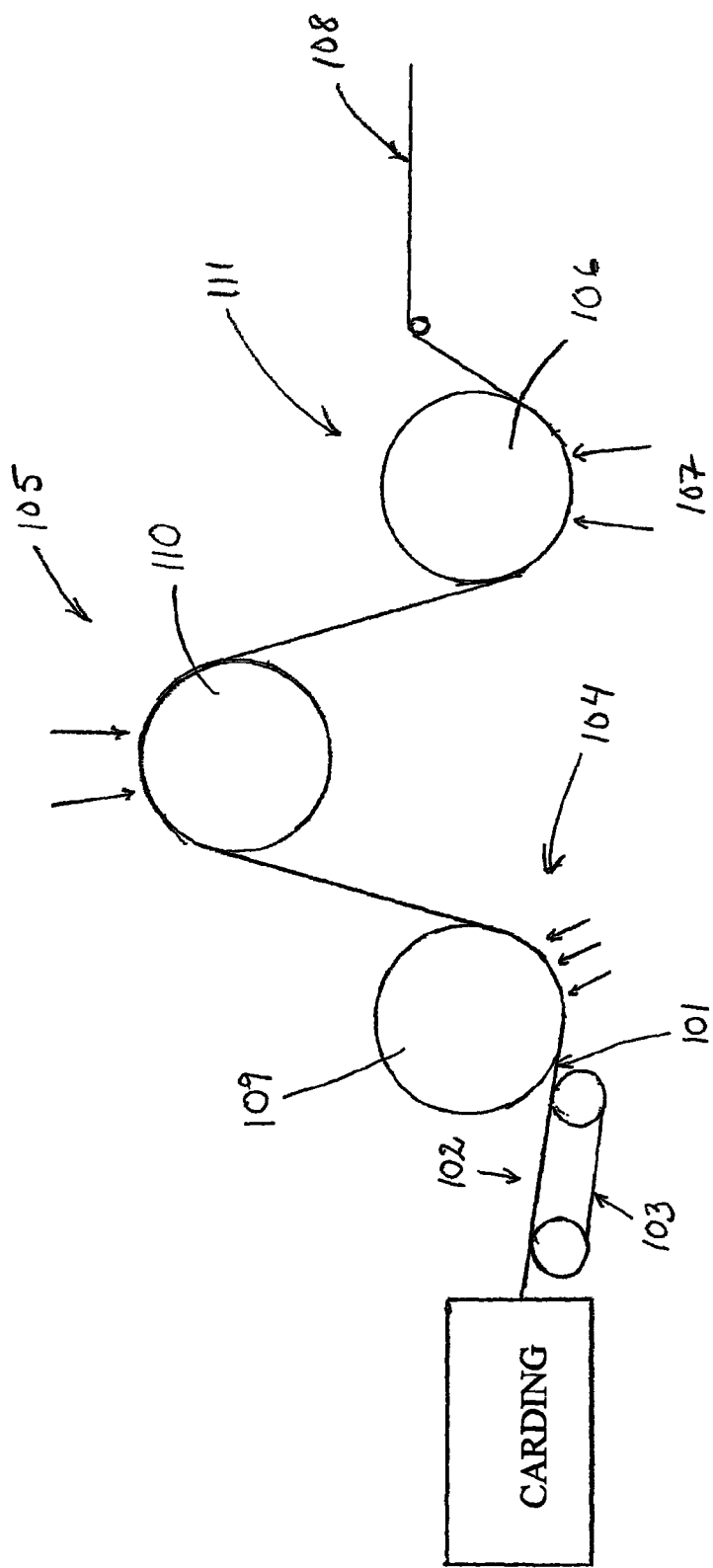
FIG. 3 illustrates schematically an embodiment of an arrangement for producing nonwoven material in accordance with the invention.

An embodiment of a nonwoven material in accordance with the invention is shown in FIG. 1. The present invention thus relates to a nonwoven material 1 for use in absorbent products, produced by hydroentangling of a substrate web comprising at least one layer of fibres selected from amongst synthetic fibres, regenerated fibres and natural fibres, wherein the nonwoven material 1 has a base level $h_0$ with protuberances 2, 3 on one side, wherein the protuberances 2, 3 constitute at least one first and one second surface structure respectively in the form of first 2 and second 3 protuberances from the base level $h_0$, wherein the first protuberances 2 have a height $h_1$ from the base level $h_0$ and the second protuberances 3 have a height $h_2$ from the base level $h_0$, wherein $h_2$ is higher than $h_1$, and each of the second protuberances 3 occupies an area of the surface of the base level at least 4 times greater than each of the first protuberances 2.

The expressions "hydroentangling" or "spunlacing" are used here to denote that fibres are tangled together by means of very fine jets of liquid under high pressure. Several rows of jets of liquid are directed at the fibre web or the substrate web, which is supported by a wire gauze or a drum. The entangled web is then dried. A nonwoven material with a well-integrated composition is obtained as a result.

Also proposed in accordance with the present invention is a method, which can be seen in hydroentangling stage 111 in FIG. 3, for producing a nonwoven material 108 by hydroentangling a substrate web 101 of fibres selected from amongst synthetic fibres, regenerated fibres and natural fibres, wherein it includes the following steps:

a) transferring the substrate web 101 to a surface-shaped carrier device 106 containing holes which form at least a first and a second pattern in the form of first and second holes respectively, wherein the second holes are at least 4 times larger than the first holes, and b) hydroentangling the substrate web 101 on the carrier device 106 by means of jets of liquid under high pressure, so that the fibres of the substrate web 101 penetrate down into the holes. The hydroentangling process utilizes conventional pressures and hole diameters in nozzles in the arrangement. Details of conventional parameters can be found in, for example, CA 841 938.

The expression "substrate web" denotes a pre-formed fibre web that is capable of being produced by one or other conventional means. Fibres are laid down onto a forming wire gauze. Continuous filaments are laid down, for example, by the meltblown or spunlaid technique, and staple fibres and pulp fibres can be wet-laid or dry-laid.

The expression "carrier device" is used here to denote the device which supports the substrate web when it is hydroentangled, and at the same time this serves the purpose of imparting an image/structure to the nonwoven material. The carrier device should be made of a material that is sufficiently hard for hydroentangling, that is to say it should be inflexible during the hydroentangling stage. Plate or nickel plate are suitable materials.

The expression "surface-shaped" denotes that the carrier device exhibits a plane and uniform surface, for example in the form of a sheet material. This can consist of a sheet of plate with holes of different sizes. The sheet has a uniform and plane surface, which we define as "surface-shaped". Holes are arranged on this surface-shaped carrier device. The sheet of plate can be formed as a drum, although it has no separate projections or depressions, but the sheet of plate is "surface-shaped" or two-dimensional with holes.

There now follows a description of an example of the production of a nonwoven material in accordance with the present invention, as illustrated schematically in FIG. 3. The substrate web 101 can be produced by carding, for example. This stage is illustrated schematically in the Figure. One or more cards form one fibre web or substrate web per card. Carding is followed by a compaction stage, for example in the form of pre-wetting 102, which compacts the material and gives it sufficient strength for further processing. A nozzle is normally used for pre-wetting. The substrate web 101 can then be provided with one or more further bonds. Pre-bonding can take place by pre-hydroentangling, as illustrated by way of example in stages 104 and 105 in FIG. 3. The substrate web 101 is then conveyed to the hydroentangling stage 111, where the substrate web 101 a) is transferred to a surface-shaped carrier device 106 containing holes which form at least a first and a second pattern in the form of first and second holes respectively, wherein the second holes are larger than the first holes, and b) is hydroentangled on the carrier device 106 by means of jets of liquid under high pressure, so that the fibres of the substrate web 101 penetrate down into the holes.

Nozzles 107 are indicated with arrows in the Figure. In the hydroentangling stage, the filaments and the fibres are mixed thoroughly together and are bonded to a nonwoven material 108 by the effect of many fine jets of liquid under high pressure, which strike the fibres in order to mix them and tangle them together with one another. The water is drained away through the holes in the carrier device 106. After hydroentangling, the nonwoven material 108 is conveyed to a drying stage (not shown). The above description of a production method is only an example. In accordance with one embodiment, dry-laid material is preferable as a substrate web.

The hydroentangling stage for the surface structure can take place alternatively on a wire gauze loop. The drum or the loop is covered with a suitable surface-shaped material containing holes in accordance with the invention and constitutes a carrier device.

Bonding can take place in one or more pre-hydroentangling stages 104, 105, which precede the hydroentangling on the carrier device 106 in accordance with the invention. Pre-hydroentangling intended for bonding of the substrate web can take place on one or both sides of the substrate web. In the case of hydroentangling on both sides, for example, two different drums 109, 110 positioned one after the other can be used, where one side of the substrate web is pre-hydroentangled on the first drum 109, and the second side is pre-hydroentangled on the second drum 110. Alternatively, pre-hydroentangling can be performed on one or more wire gauze loops. The nozzles on the drums 109, 110 are indicated in the form of arrows.

The number of nozzles per drum is around 1 to 3, although a larger number of nozzles can also be present.

When specific materials or compositions of materials are used, pre-bonding of the substrate web, for example in the form of pre-hydroentangling, may be necessary. The substrate web must hold together sufficiently well to enable it to be moved to the hydroentangling stage on the carrier device when the substrate web is to be given its surface structure.

The carrier device can be manufactured from a metal plate or a sheet of sufficient hardness to enable it to function as a support in conjunction with hydroentangling. The plate or the sheet must exhibit a plane and uniform surface, and it must contain the holes that are intended to impart the surface structure. It is preferable for the carrier device to be formed as a cylinder.

A nonwoven material in accordance with the invention is obtained by the new method. A nonwoven material of this kind exhibits protuberances of different heights, and these protuberances occupy different areas of the surface of the base level of the nonwoven material. This results in a good liquid distribution, absorption capacity and good comfort during use, advantages that are described in greater detail below.

The hydroentangling of the fibres causes the quantity of fibres to vary between protuberances with a different height and surface extent in the base level and the material in the rest of the nonwoven material. The expression "rest of the nonwoven material" is used to denote those parts that lie between the protuberances in the extent of the plane of the nonwoven material. The variation in the fibres depends both on the pressure in the jets of liquid and on the composition of the fibres in the material. Different fibres are caused to move with greater or less ease by the act of spraying liquid against the substrate web on the carrier device. Shorter fibres are able to move more easily, for example. This results in a nonwoven material with a good capacity to absorb different liquids. Hydroentangling also results in the creation of a strong nonwoven material.

In accordance with previously disclosed hydroentangling, the image transfer surface has had depressions and/or projections of the kind disclosed in WO 02/04729, for example. An image transfer surface of this kind can be regarded as three-dimensional. When nonwoven material is formed against a depression in the image transfer surface, a depression is formed on one side and a corresponding raised area on the other side. The opposite applies in the case of forming against a projection on the image transfer surface. A carrier device which transfers surface structures to the nonwoven material is used with the invention. The carrier device can be a plate, for example a nickel plate. The carrier device can be extended as a web or can form a drum. Compared with previously disclosed technology, which utilizes a three-dimensional image transfer surface, the carrier device in accordance with the invention is regarded as being surface-shaped or two-dimensional in the sense that it does not exhibit any projections or depressions. In the case of a plate, it consists of a sheet of plate with holes of different sizes. The sheet of plate can be formed as a drum, although it does not possess any separate projections or depressions. Described in WO 03/083197, as previously mentioned, is a method for hydroentangling on a plastic gauze which contains holes. In conjunction with this, protuberances with the same height and size are produced in the nonwoven material. According to the present invention, protuberances are produced where the second protuberances occupy an area of the base level at least 4 times larger than in the case of the first protuberances, where the protuberances have different heights. Images of this kind in a nonwoven material are not produced in WO 03/083197.

Before hydroentangling takes place, in which the surface structure is produced, pre-hydroentangling can be performed as described above. In conjunction with this, pre-hydroentangling is able to cause bonding together of the substrate web, which can take place on both sides of the substrate web.

In the course of the hydroentangling, for the purpose of forming the surface structure, water or some other liquid is sprayed at high pressure onto the substrate web that is supported against the carrier device. These water jets bring about entangling of the substrate web, that is to say tangling together of the fibres. A nonwoven material with a well-integrated composition is produced. The appropriate pressure in the entangling nozzles is adapted according to the fibre material, the weight per unit area of the substrate web, etc. The fibres in the substrate web will become tangled together, that is to say the nonwoven material is bonded together, at the same time as a surface structure is formed on the nonwoven material. The pressure exerted by the water jets is so high that the fibres are caused to be displaced on the carrier device, and they will penetrate down into the holes. The ability to penetrate down into the holes depends in part on the physical size of the holes. A larger hole will permit the fibres to penetrate further down into the holes. This results in protuberances with different heights $h_1$ and $h_2$ in the nonwoven material. Dewatering takes place in conjunction with the forming of the protuberances, and the water is drained away through the same holes in which the protuberances are formed. This results in the fibres moving easily on the carrier device and being displaced towards the holes and down into the holes.

The fibres on the carrier device that are present in association with the fibres that are drawn down into the holes will accompany them, and this will lead to the resulting other side of the nonwoven material exhibiting an essentially smooth surface.

The nonwoven material is used in accordance with the present invention preferably as a surface layer in an absorbent product.

The use of hydroentangling of the nonwoven material to impart surface structures produces a softer and more textile-like material with good strength characteristics. The tangling together of the fibres in the hydroentangling process provides a good mechanical bond between the fibres, and good strength of the nonwoven material is achieved in this way. Moreover, the fibres are not damaged by thermal embossing, for example. A soft and textile-like material is of great importance for absorbent products, for example of the kind that will be placed inside panties, knickers or underpants. The absorbent product must be visible as little as possible, in view of the desire to be able to wear the absorbent product discreetly. The textile-like appearance is very advantageous in this case. Softness and smoothness are also an important factor for a product that will lie against the wearer's skin.

At least two surface structures in the form of two protuberances 2, 3 are contained in nonwoven material, one background structure and one principal structure. The protuberances in the surface structures have different heights $h_1$ and $h_2$. The background structure has a lower height $h_1$, since it is not intended to be the predominant surface structure.

The different heights of the surface structures mean that the base level of the nonwoven material will not always come into direct contact with the wearer's skin. The surface layer in the form of nonwoven material will have a number of different levels above the base level of the nonwoven material. In the first place, the protuberances of the principal structure with the greater height $h_2$ will come into contact with the wearer's skin. Reduced contact with the skin means that the product will sit more airily on the wearer, and an increased flow of incoming air will be achieved between the product and the body. Moisture that has been absorbed from the product and may continue to be present in the surface layer will also not come into contact with the wearer's skin to the same extent. This results in better comfort.

The fact that the protuberances occupy areas of different sizes results in the surface structures with the larger and higher protuberances being more clearly visible than the first surface structures, which may be regarded as a background structure.

Good absorption capacity and liquid distribution are also obtained with the help of the various protuberances. The quantity of fibres will vary between different protuberances of different heights and the material outside the protuberances. This in turn leads to different pore sizes in different areas of the nonwoven material. The pore volume distribution that is present on the side with a surface structure is thus broader than on a surface without a surface structure and protuberances or with only a single surface structure. Larger pores have the ability, for example, to contribute to the better absorption of highly viscous substances such as menstrual fluids. In accordance with the present invention, the second protuberances occupy an area of the surface of the base level of the nonwoven material at least 4 times greater than the first protuberances. The protuberances with a height $h_2$, that is to say with the highest height, occupy the greatest area. This results in protuberances that are larger, in terms of both their height and their extent. These protuberances exhibit excellent absorption, in particular of highly viscous substances, and the nonwoven material will possess very good absorption characteristics. The larger areas of the protuberances also lead to significant differences in the appearance of the different surface structures. A soft and pliable material is also obtained in accordance with the invention, at the same time as it is smooth and flexible, due to the fact that the nonwoven material is hydroentangled. The fourfold difference in size accordingly gives rise to, among other things, protuberances with a different pore size distribution, which has a positive effect on liquid absorption and the distribution of the liquid in the nonwoven material.

One of the purposes of the surface structures is to be decorative. The protuberances in the surface structure can have any desired form. The protuberances can be circular, elliptical, triangular, square, etc. These can also be combined to form an image, for example flowers, hearts, leaves, feathers, etc. This may be a logotype, for example, or some kind of information for the wearer that may be of assistance in relation to the method of use. A more refined product is obtained with two different surface structures. On the one hand, a distinct image is obtained in the form of the principal structure. The background structure provides a more complete image of a product, with a textile-like appearance that imparts a better feel than a smooth material. This gives the impression of increased absorption and strength. A more airy product is obtained in addition, which reduces the area of contact with the body.

Figure 4:
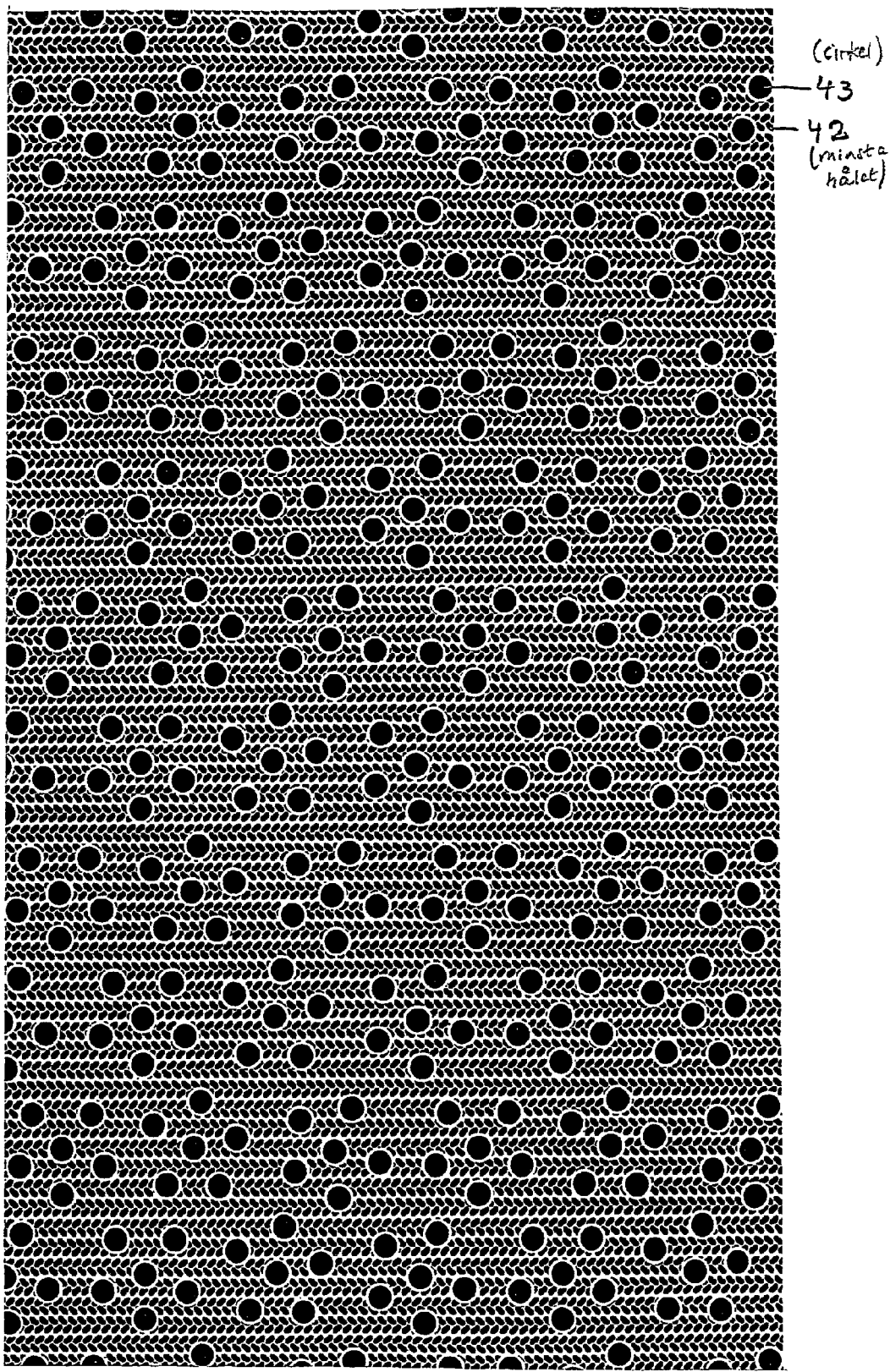
FIG. 4 illustrates an embodiment of a plate of a carrier device viewed from above, which is used in the method in accordance with the present invention.

An embodiment of a plate that is used in accordance with the invention is shown here in FIG. 4 to illustrate how the holes are distributed over a plate. In order to illustrate the plate, the holes are indicated as black, and the plate itself is white in the Figure. Illustrated here are the smaller holes 42, which constitute the first holes 42 which form the first pattern, and the larger holes 43, which constitute the second holes 43 and form the second pattern. The second pattern thus constitutes the circular holes 43, which are grouped in a regular pattern, although this is not essential for the invention. An irregular pattern can also be possible. The first pattern is the background pattern, which consists of the small holes 42, which can also be a regular or an irregular pattern. The protuberances that are formed against the smaller holes 42 will constitute a background structure in the nonwoven material in accordance with the present invention, while the protuberances that are formed against the larger holes 43 will constitute a principal structure.

In accordance with the method, the carrier device contains holes 42, 43 which form patterns, whereas the nonwoven material contains protuberances 2, 3 which form surface structures. The patterns and the surface structures correspond to one another in the sense that the pattern that is present on the carrier device creates the surface structure on the nonwoven material. The first and the second pattern respectively will provide the first and the second surface structure of the nonwoven material.

In accordance with the invention, the second side of the nonwoven material is essentially smooth. As can be appreciated from FIG. 1, the smooth side can be regarded as a bottom level B in the nonwoven material in relation to the base level $h_0$ and the protuberances 2, 3 on the first side. When the nonwoven material is utilized in an absorbent product, it is usually glued to the subjacent layer. If the nonwoven material in accordance with the invention is used as a surface layer in an absorbent product, its side with surface structures or protuberances is usually turned to face towards the wearer during use. This means that the smooth surface faces away from the wearer and downwards in the absorbent product. When the nonwoven material is utilized in the product, it may be glued securely to a subjacent layer, for example. It is then an advantage if the side that will be stuck to another layer is essentially smooth. Good contact is achieved between the two layers. If adhesion is obtained only with beads of adhesive, good contact will still be achieved, because at least one of the surfaces to be glued is smooth. Good contact between the layers also provides an advantage for the liquid distribution inside the product. Liquid from the upper layer is distributed more easily to the lower layer if good contact is present between the layers.

In the nonwoven material in accordance with the present invention, each of the second protuberances occupies an area of the surface of the base level at least 4 times greater than each of the first protuberances. This is achieved by the method in accordance with the present invention, wherein the second holes are at least 4 times larger than the first holes. A certain difference in size between the holes in the carrier device is required in order for a difference in height to be capable of being achieved in the protuberances in the nonwoven material. On the basis of the at least fourfold difference in size, this gives the difference in height that is sought in accordance with the present invention. The resulting nonwoven material exhibits advantageous absorption characteristics thanks to the pore volume distribution and the protuberances of different sizes, and the surface structures will be particularly clearly visible thanks to the difference in sizes. The greater the relationship that exists between the area of the base level occupied by the first protuberances and the second protuberances, the greater will be the difference in height between the protuberances, and the better will be the effects that can be achieved, that is to say better pore size distribution, better absorption, and even more distinct patterns. The geometrical design of the holes can govern the differences in height to a certain extent. For example, a narrow and elongated hole will be lower than a symmetrical hole if these occupy the same area. According to further embodiments, each of the second protuberances can occupy an area of the surface of the base level at least 8 times greater than each of the first protuberances in the nonwoven material in accordance with the present invention, and it is more preferable still for the second protuberances to occupy an area of the surface of the base level at least 12 times greater than each of the first protuberances. The second holes in the method can be at least 8 times larger than the first holes, and it is more preferable still for the second holes to be at least 12 times larger than the first holes. This leads to good liquid distribution in the nonwoven material, and the second surface structure will be particularly clearly visible. The greatest difference in size is in the order of 50 times, although even ca. 80 times larger may be possible, with regard to both the hole size and the area of the protuberances.

The height $h_1$ of the nonwoven material in accordance with the invention is preferably at least 200 μm, and the height $h_2$ is preferably at least 300 μm. In accordance with a preferred embodiment, the difference between $h_1$ and $h_2$ is at least 100 μm, and it is more preferable still for the difference between $h_1$ and $h_2$ to be at least 200 μm. These heights and this difference in height provide good airiness against the wearer's skin, which offers good comfort. Good liquid distribution and absorption are also obtained. Highly distinct surface structures and particularly distinct differences are also obtained between the background structure and the principal structure.

The first protuberances preferably occupy an area of the surface of the base level of at least 0.25 mm² or thereabouts. A size of 0.25 mm² is required in order to be able to provide a background structure. The largest size is about 1.00 mm². Each of the second protuberances also occupies an area of the surface of the base level preferably of at least about 1.00 mm², which is four times 0.25, and the size of 1.00 mm$^2$ is required in order to be able to produce the desired effects. The second protuberances can have sizes of about 4-16 mm$^2$. They can also be as large as 20 mm$^2$. If the first protuberance occupies an area larger than 0.25 mm$^2$, the second protuberances will in turn occupy a larger area in order for the same effects to be capable of being achieved, that is to say at least 4 times larger than the area of the background pattern.

In accordance with the method, the second holes in the carrier device preferably have a size of at least about 1.25 mm$^2$, and the first holes preferably have a size of at least about 0.25 mm$^2$. The desired heights in the protuberances in the nonwoven material in accordance with the invention are achieved at these orders of size. Additional hole sizes correspond to the sizes of the protuberances referred to above.

Figure 5:
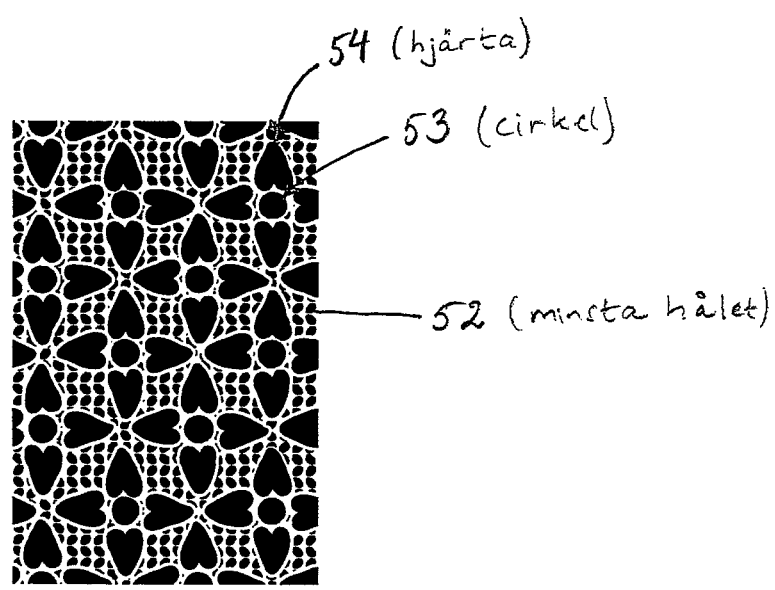
FIG. 5 illustrates a further embodiment of a plate of a carrier device viewed from above, which is used in the method in accordance with the present invention.

The nonwoven material in accordance with the present invention can have additional protuberances 24, FIG. 2, with at least an additional height $h_2^1$ from the base level $h_0$, wherein the height $h_2^1$ of the additional protuberance 24 is greater than $h_2$ and occupies a larger area of the surface of the base level than the protuberances 23 with the height $h_2$. An embodiment of this kind is illustrated in FIG. 2, for example. The nonwoven material has first protuberances 22 with a height $h_1$ and second protuberances 23 with a height $h_2$. Also present is a third protuberance 24 with a height $h_2^1$ that is higher than $h_2$, which constitutes a part of the second surface structure, that is to say it constitutes a part of the principal structure. Illustrated in FIG. 5 is a plate with the ability to produce a nonwoven material having three protuberances with the heights $h_1$, $h_2$ and $h_2^1$. A background pattern with smaller holes 52 is shown here. The larger holes constitute circular holes 53, which constitute a part of the principal pattern, which in this case is a floral pattern. The principal pattern also includes additional holes 54, in this case heart-shaped holes, of a size that is larger than the size of the holes 53. These constitute a part of the principal pattern. Present on a plate of this kind are protuberances with the height $h_1$ formed against the small holes 52, protuberances with a height $h_2$ formed against the holes 53, and protuberances with a height $h_2$ formed against the holes 54.

A nonwoven material containing protuberances with the additional height $h_2^1$ is produced in accordance with the method, where the carrier device has additional holes which are larger than the holes in the second patterns.

The nonwoven material 1 in accordance with the invention can also have additional protuberances 25 having at least an additional height $h_1^1$ from the base level $h_0$, wherein the height of the additional protuberance 25 is lower than $h_1$ and occupies a smaller area of the surface of the base level than the protuberances 22 with the height $h_1$. The protuberances 25 can also been seen in FIG. 2. A nonwoven material of this kind comprising additional protuberances with the height $h_1^1$ is produced in accordance with the method, in which the carrier device has additional holes that are smaller than the holes in the first patterns. Different sizes of the holes give different heights of the protuberances. The larger the hole, the higher the resulting protuberance.

Protuberances with heights between $h_1$ and $h_2$ can also occur, of course.

Additional surface structures can also be formed by protuberances with a different height and which occupy a different area of the surface of the base level than the protuberances with the heights $h_1$ and $h_2$. More different heights provide an even broader pore size distribution, which is beneficial for the absorption capacity and the ability to retain highly viscous substances in the protuberances. It will also be possible to distribute contact with the wearer's skin among the various surface structures, which provides comfort for the wearer. More advanced surface structures can be created in addition. This also contributes additionally to imparting a more textile-like appearance, which is very positive in products of this type.

The carrier device 109 can also have additional holes which are smaller than the holes in the first patterns. The nonwoven material obtained in this case comprises additional protuberances with a height $h_1^1$ that are lower than the protuberances with a height $h_1$.

Nonwoven material in accordance with the invention can comprise synthetic fibres, which are selected from amongst polyolefin, polyester and polyamide fibres and mixtures thereof. The polyolefins, for example, are polyethylene or polypropylene. An example of a polyester is polyactide. The fibres can be produced from homopolymers or copolymers or mixtures thereof. The material for the synthetic fibres can also be selected from amongst mono-, bi-, multi-components and mixtures thereof. These materials and types of fibres are suitable for use in nonwoven material that constitutes the surface layer in absorbent products.

The fibres can also include regenerated fibres, which can be selected from amongst regenerated cellulose fibres such as rayon, viscous and lyocell.

The synthetic fibres are selected from amongst staple fibres, continuous filaments and mixtures thereof. Hydroentangling of fibres can be performed with both staple fibres and continuous filaments. An advantage associated with shorter fibres is that it is easier to create the desired surface structures. Continuous filaments require larger holes in the carrier device in order to be able to form protuberances.

Meltblown or spunlaid fibres are preferably selected from amongst the continuous filaments, and the most preferred are spunlaid fibres. They should preferably possess a coarseness of 1-3 dtex. The cross section of the fibres can be circular or trilobal, for example. Other cross sections are also conceivable.

When continuous filaments are used, the substrate web should preferably not be thermally bonded. The filaments will then be capable of being displaced more readily on the carrier device and of being laid down and penetrating down into the holes in the carrier device in conjunction with the entangling process. In spite of the preference for non thermally-bonded continuous filaments, the method will still function if the filaments are thermally bonded. Non-bonded filaments on the substrate web are achieved by cooling the fibres in conjunction with laying down to form a substrate web, so that they solidify before they come into contact with one another.

The staple fibres preferably have a length of at least 3 mm. Fibres with lengths of less than 3 mm are difficult to hydroentangle. They should preferably have a length not exceeding 60 mm, or not exceeding 50 mm. In a preferred embodiment, they have a length of at least 30 mm. The staple fibres preferably possess a coarseness of 1-3 dtex. If thin fibres are used, the length of the fibres should be quite short. Otherwise, the risk is present that the fibres will become tangled together in clumps. The cross section of the fibres may be circular, trilobal, star-shaped, hollow, etc.

The fibres can include micro fibres in the form of split fibres that are split at the hydroentangling stage, both continuous filaments and staple fibres, which possess a coarseness of less than 1 dtex. Such fine fibres give a smooth and soft product.

Nonwoven material in accordance with the invention can include natural fibres, which are selected from amongst cellulose fibres, pulp fibres, cotton fibres, ultimate flax fibres and mixtures thereof.

If the nonwoven material contains pulp fibres, they will be present in a higher proportion in the protuberances than in the rest of the nonwoven material. This is because these fibres are more mobile and exhibit the ability to participate in the entangling when the fibres are sprayed with water jets. Pulp fibres are irregular, flat, twisted and wavy, and they become pliable when wet. These characteristics mean that they can be easily mixed into and entangled with a web of continuous filaments and/or staple fibres. Pulp fibres and regenerated fibres also possess a low wet module, with the result that they are easier to bend in the wet condition. This is of benefit for hydroentangling. The resulting nonwoven material will thus contain a higher proportion of pulp fibres in the protuberances, with the highest proportion being present in the protuberances with the highest height and the largest area extent in the base level. Rapid absorption can thus take place when the protuberances come into contact with body fluid, for example, that will be absorbed into, for example, a hygiene product such as a sanitary towel. These protuberances absorb well, since pulp fibres are highly absorbent and the protuberances can exhibit large pores, which is advantageous with regard to highly viscous fluids. Because pulp fibres are more opaque than synthetic fibres, for example, the proportionate increase in the protuberances will also result in the protuberances being much more clearly visible and in the production of a distinct image on the nonwoven material. The proportionate increase in pulp fibres in the protuberances also leads to a rapid and increased absorption capacity in the protuberances.

The total density of the fibres, which is measured in $g/cm^3$, may be lower in the protuberances. This is attributable to the fact that the hydroentangling process has not displaced sufficient fibres into the holes in the carrier device to compensate for the expansion that has taken place, with the result that the density is lower in the protuberances. The expression "expansion" is used here to denote that the fibres have been able to expand into the holes in the plate and, in so doing, into the protuberance in the material. Different fibres are displaced with different ease in conjunction with hydroentangling. Pulp fibres, for example, are displaced very easily, whereas longer fibres or continuous filaments may find it more difficult to be displaced into the holes. The resulting nonwoven material will then have wider pores in the protuberances, which is advantageous for the absorption of highly viscous liquids.

Nonwoven material can also include other ingredients in the form of polymers, additives, etc.

Preferred weights per unit area for the nonwoven material in accordance with the invention are at least 30 $g/cm^3$, or preferably 60 $g/cm^3$. The weight per unit area preferably does not exceed 120 $g/cm^3$, or more preferable still 100 $g/cm^3$. A relatively high weight per unit area is required in order to be able to create a distinct surface structure. The most preferable weight per unit area is ca. 80 $g/cm^3$.

In a preferred embodiment of the invention, the nonwoven material contains 20-80% by weight of lyocell fibres having a coarseness of 1.5-2 dtex and a length of 30-40 mm, and 80-20% by weight of polyethylene terephthalate fibres having a coarseness of 1.5-2 dtex and a length of 30-40 mm.

In accordance with one embodiment, the nonwoven material can contain 20-80% by weight of viscose fibres or lyocell fibres and 80-20% by weight of synthetic fibres. Synthetic fibres are selected from amongst polypropylene, polyamide, polyethylene and polyester fibres. An example of polyester fibres is polyethylene terephthalate fibres.

The invention also includes nonwoven material containing fibres in several layers. These may be layers containing a number of different fibres or the same sort of fibres. A plurality of such layers may also be used to form a laminate. In the method in question, this means that the substrate web comprises several layers, or that several layers of substrate webs are transferred to the carrier device for hydroentangling.

The layers can be carded, and each can come from its own carding machine, in conjunction with which they are joined together in the hydroentangling stage at the same time as an image is produced on one side. The first layer, which can be regarded as a carrier material, consists solely of polyethylene terephthalate and is laid down nearest the drum and constitutes that side of the nonwoven material that will be patterned, and the second layer will lie above the first layer, the carrier material, during the hydroentangling stage. With the hydroentangling method that is used, with the drum as the base for producing the image or decoration, it is advantageous for regenerated fibres to be hydroentangled down into the carrier material and, in so doing, to form the desired three-dimensional surface structures. Pulp fibres or regenerated fibres bend more easily, which can be attributed to their low wet module. In this case, the carrier material is the first layer, on top of which the next layer is laid. The method described here in respect of different layers and carding is only one example of how a substrate web can be produced. Other types of fibres can be used, for example. The layers can also arrive in a different sequence, or the web can be turned during the process so that the top layer is patterned.

Figure 9:
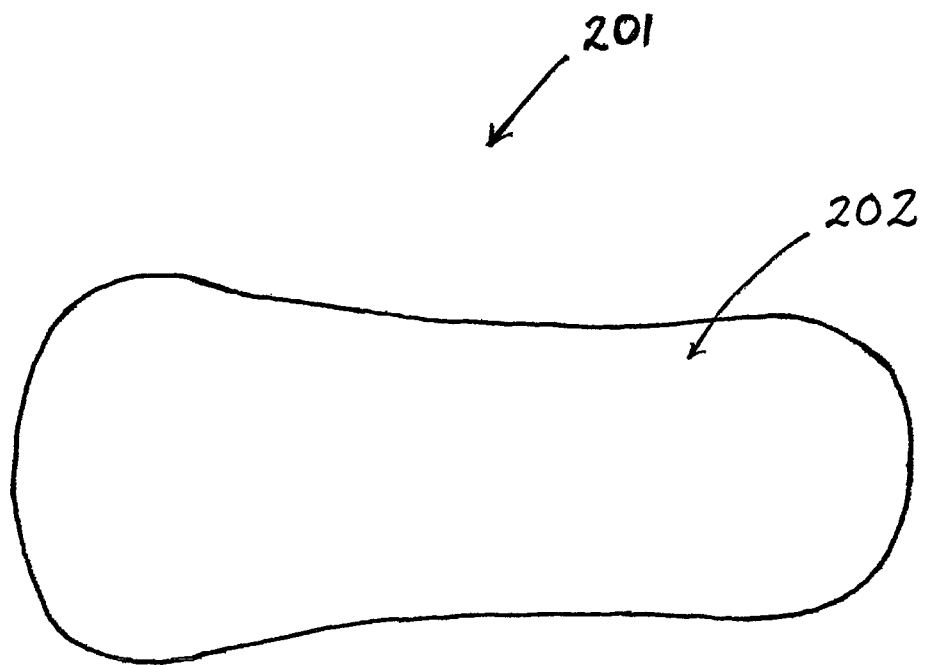
FIG. 9 shows an embodiment of a sanitary towel viewed from above.

In accordance with the present invention, the proposed absorbent product also comprises a surface material and a backing layer, in conjunction with which it comprises a nonwoven material as the surface layer, where the nonwoven material is a nonwoven material described in accordance with the above. Illustrated in FIG. 9 is an embodiment in the form of a sanitary towel 201 comprising a nonwoven material as the surface layer 202. Also included is a backing layer, which is not shown here, and possibly interjacent layers as described below. The nonwoven material has a base level with protuberances on one side, wherein the protuberances form at least a first and a second surface structure respectively in the form of first and second protuberances from the base level, wherein the first protuberances have a height $h_1$ from the base level and the second protuberances have a height $h_2$ from the base level, where $h_2$ is higher than $h_1$, and each of the second protuberances occupies an area of the surface of the base level at least 4 times greater than each of the first protuberances.

The backing layer can consist of a flexible film, for example a plastic film. Examples of plastic materials in the film are polyethylene (PE), polypropylene (PP), polyester or some other suitable material, such as a hydrophobic nonwoven layer or a laminate of a thin film and a nonwoven material. These types of material are often used in order to achieve a soft and textile-like surface on the backing layer. The backing layer can be breathable, so that it permits vapour to pass through while also preventing penetration by liquid. The breathable materials can consist of porous polymer films, nonwoven laminates produced from spunbonded and meltblown layers, and laminates produced from porous polymer films and nonwoven materials.

The backing layer can have an adhesive attachment in the form of beads of adhesive, for example, on the side of the backing layer that faces away from the surface layer, to enable them to be secured in panties, underpants or knickers. A release material may be applied on top of the adhesive in order to protect the adhesive when the product is not in use.

The absorbent product can also comprise an absorbent core or structure between the surface layer and the backing layer. The absorbent core can be constructed from one or more layers of cellulose fibres, for example cellulose fluff pulp, airlaid, fluff pulp, dry defibred or compressed pulp. Other materials that can be used include, for example, absorbent nonwoven material, foam material, synthetic fibre material or peat. Apart from cellulose fibres or other absorbent materials, the absorbent core can also comprise superabsorbent materials, so-called SAP (superabsorbent polymers), which are materials in the form of fibres, particles, granules, films or the like. Superabsorbent polymers are inorganic or organic materials that are capable of swelling in water and are insoluble in water, which exhibit the capacity to absorb at least 20 times their own weight of an aqueous solution containing 0.9% by weight of sodium chloride. Organic materials that are suitable for use as a superabsorbent material can include natural materials such as polysaccharides, polypeptides and the like, as well as synthetic materials such as synthetic hydrogel polymers. Such hydrogel polymers can include, for example, alkaline metal salts of polyacrylic acids, polyacrylamides, polyvinyl alcohol, polyacrylates, polyacrylamides, polyvinyl pyridines and the like. Other suitable polymers include hydrolysed acrylonitrile-grafted starch, acrylic acid-grafted starch, and isobutylene maleic acid anhydride copolymers and mixtures thereof. The hydrogel polymers are preferably readily cross-linked to ensure that the material remains essentially insoluble in water. The preferred superabsorbent materials are also surface cross-linked so that the external surface or the shell of the superabsorbent particle, fibre, sphere, etc., has a higher cross-linking density than the inner part of the superabsorbent. The proportion of superabsorbents in an absorbent core can be between 10 and 90% by weight, or preferably between 30 and 70% by weight.

The absorbent core can comprise layers of different materials with different characteristics with regard to their ability to receive liquid, liquid distribution capacity and storage capacity. The absorbent core is more often than not extended in the longitudinal direction and can, for example, be rectangular, T-shaped or hourglass-shaped. An hourglass-shaped core is wider in the front and rear parts than in the crotch part, in order to provide effective absorption, at the same time as the design makes it easier for the product to be formed close to and around the wearer, thereby providing a better fit around the legs.

The absorbent product can also include a transport layer between the surface layer and the absorbent core. The transport layer is a porous, flexible material and can comprise one or more of the following: airlaid, wadding, tissue, carded fibre web, superabsorbent particles or superabsorbent fibres. A transport layer has a high instantaneous capacity to receive liquid and is able to store liquid temporarily before it is absorbed by the subjacent absorbent core. The transport layer can cover the whole or parts of the absorbent core.

The surface layer, the backing layer and any interjacent materials are sealed at the edges of the product, which can be effected by thermal sealing, for example, or by some other conventional means.

The absorbent product can also comprise wings on its sides. It can also comprise elastic in order to provide better contact with the body when the product is being worn, and also to reduce leakage.

EXAMPLES

There now follow a number of examples of nonwoven materials produced in accordance with the present invention. A substrate web is produced in the conventional way. The substrate web is then hydroentangled, wherein it is transferred to the carrier device in the form of a plate that is cylindrical in shape. The substrate web is hydroentangled with jets of water.

A number of different plates are used in production. Data for the background patterns of these plates are shown in Table 1. The area of individual holes in the background pattern has been measured. The individual holes can form part of an image, for example a flower. One example of a part of an image is illustrated below for a principal pattern in FIG. 5. If the background pattern contains a group of protuberances with different areas, which together constitute part of an image, for example a flower, these protuberances together constitute part of an image of a first surface structure that has been produced on a group of holes in a first pattern. The area of part of an image has also been measured.

Data for the principal patterns of these plates are shown in Table 2. The area of individual holes in the principal pattern has been measured here. Here the area has been measured for the largest holes. The individual holes can form part of an image, for example a flower. If the principal pattern contains a group of protuberances with different areas, which together constitute an image, these protuberances together constitute part of an image of a second surface structure that has been produced on a group of holes in a second pattern. Part of an image of a second surface structure in the form of a flower is illustrated in FIG. 5, for example. The area of part of an image has also been measured.

Table 3 shows the size relationship between holes in the principal pattern and the background pattern, that is to say between the second pattern and the first pattern. The size relationships are shown in respect of individual holes/individual holes.

Heights $h_1$ and $h_2$ measured in the nonwoven material that was produced on these plates are shown in Table 4. The difference in height $h_2-h_1$ is also shown in Table 4.

Nonwoven materials A, B, C and D produced on plates 1, 2, 3 and 4 are a nonwoven material comprising two layers. The first layer contains 100% by weight of polyethylene terephthalate and has a weight per unit area of 25 g/m$^2$. The fibre coarseness is 1.7 dtex, and the fibre length is 38 mm. The second layer contains 72% by weight of lyocell fibres and 28% by weight of polyethylene terephthalate. These fibres also have a coarseness of 1.7 dtex and a length of 38 mm. Nonwoven materials E and F produced on plates 5 and 6 have a fibre composition of 60% by weight of Vigor Fluff sulphate pulp from Korsnäs, 23% by weight of polyester (PET) with a length of 20 mm and a coarseness of 1.7 dtex, and 17% by weight of polypropylene fibres (PP) with a coarseness of 1.7 dtex. The weight per unit area is 80 g/m$^2$.

The heights were measured with a contact-free method of measurement. The equipment used is known as MicroProf and is supplied by FRT (Fries Research & Technology). A sensor H1 is used, and a vertical resolution of 3000 µm was used. The resolution in the vertical sense (z-axis) is 100 nm. A description of the method of measurement follows below.

The test specimen is positioned horizontally on a measurement table, where it is held in place by negative pressure. The surface is then illuminated with focussed white light. A passive lens with high colour deviation spreads out the white light vertically in different colours with different focal points and, accordingly, at different heights above the test specimen. When the focussed light meets a surface, it is reflected optimally unlike the unfocussed light, which has a more diffuse reflection. The optimally reflected light passes via the aforementioned lens and an optical cable into a miniature spectrometer. The miniature spectrometer determines the wavelength (colour) of the reflected light, and the distance between the sensor and the test surface is determined with the help of an internal calibration table. The measurements are performed on an area of 20×20 mm with a resolution of 187 measurement points/cm. The diameter of the light beam (measurement point) under these conditions is 5-6 μm.

Figure 6:
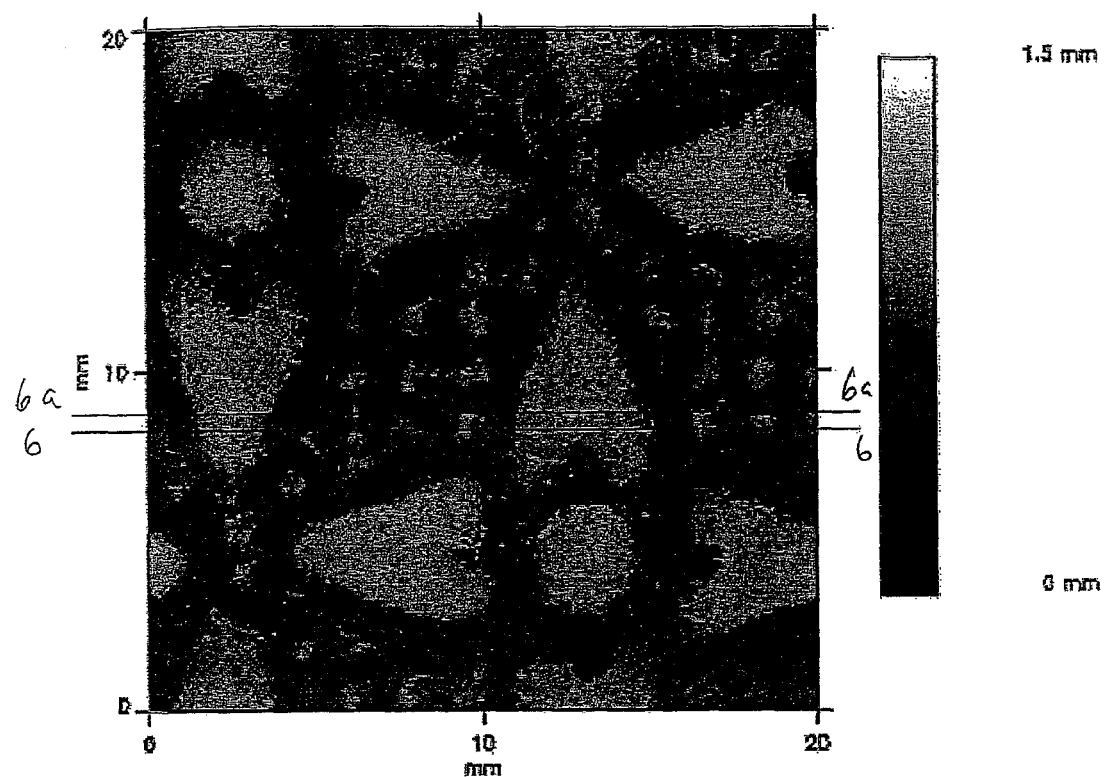
FIG. 6 shows a two-dimensional optical representation of a nonwoven material viewed from above.
Figure 7:
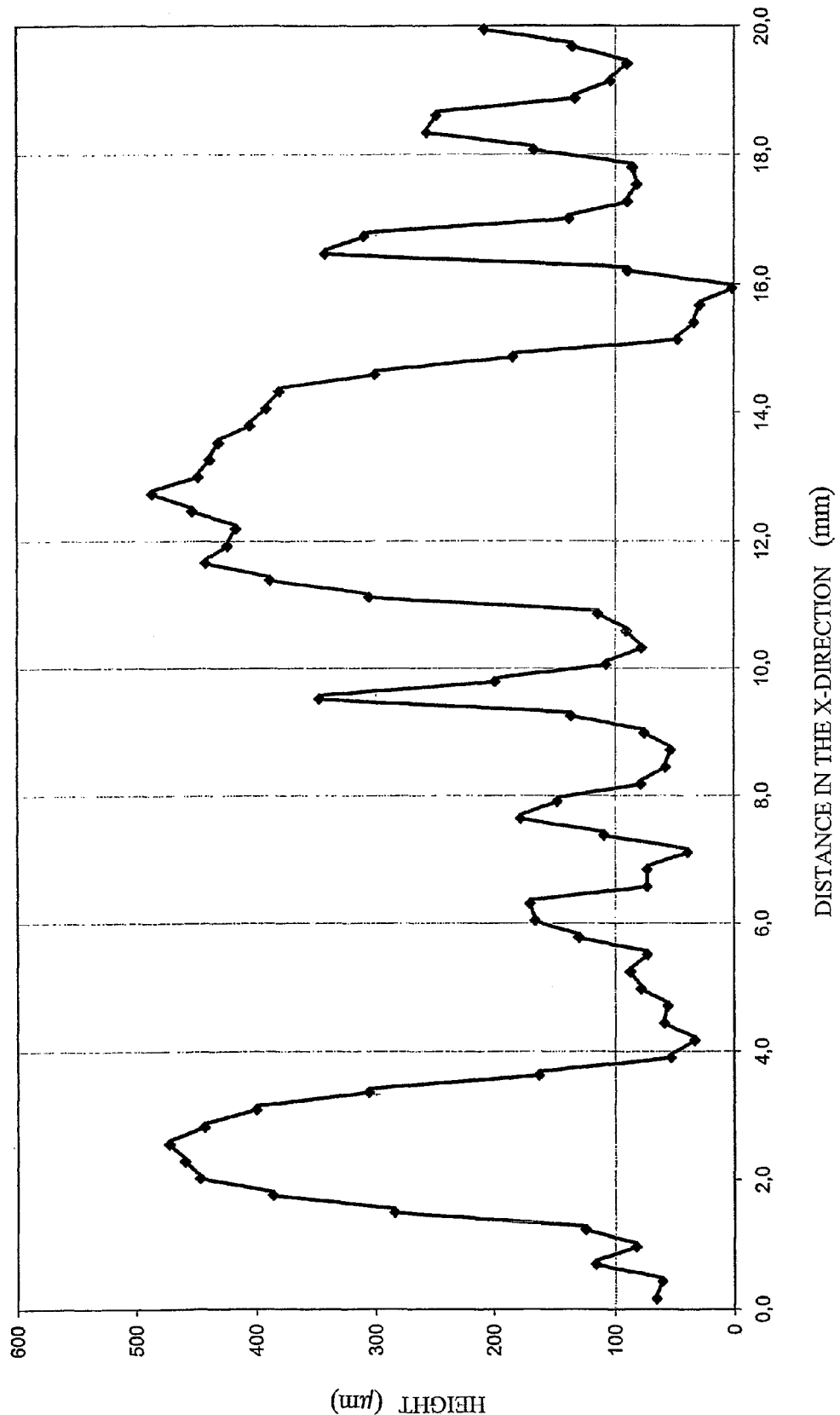
FIG. 7 shows a profile curve of the nonwoven material in the cross section between 6-6 and 6a-6a in FIG. 6.

Every image that illustrates 20×20 mm of the surface of a material is built up of 139876 measurement points, with 374 measurement rows in the y-axis and 374 measurement points on each measurement row. A section of 0.5 mm in the y-axis for the various patterns was studied, that is to say the profile curve, which illustrates differences in height in the material, reflects an area with a width of 0.5 mm in the y-axis. The two-dimensional optical image in FIG. 6 shows an example of how a section is drawn, and the profile curve in FIG. 7 shows the surface profile of the material between the two solid lines 6-6 and 6a-6a.

In order to avoid the effect of individual fibres and fibre bunches that are oriented in the y-axis of the image and project up from the surface of the material and have nothing to do with the actual surface profile, the individual mean values for y, on which the profile curve is based, have been smoothed in respect of their mean value. This smoothing of the mean value also contributes to eliminating the sharp, deep troughs that occur in the profile curve. These sharp troughs have their origin in hollow spaces between the fibres in the porous nonwoven material, and these, too, have nothing to do with the actual surface profile. Smoothing of the mean value is performed on five mean values for y in the x-axis. Smoothing of the mean value of a greater number of values than five results in a loss of information, that is to say the height of the peaks in the profile curve is lost, and smoothing of the mean value of a smaller number of values than five fails to provide satisfactory elimination of the sharp peaks and the deep troughs that occur. The effect of fibres and fibre bunches that are oriented in the x-axis of the image is eliminated thanks to the fact that the section that is being observed is broader (0.5 mm) than the width of these fibres and fibre bunches. Because the background pattern in certain cases occupies small areas of the base level, a section broader than 0.5 mm should not be selected in view of the associated risk of measuring outside the actual protuberance and the resulting values that are too low.

Profile curves have been drawn at three different points on all of the material images in order to determine the height of the protuberances in the background structure and the principal structure. The mean value of these three measurements is shown for the respective materials in the accompanying Table. Profile curves have been drawn on distinct background and principal structures, and the height $h_2$ has been measured here at a maximum height of a lowest protuberance in the profile curve. $h_1$ has been measured at the maximum height of the protuberance in the background structure.

TABLE 1 background pattern

| Plate designation | Form | Area (mm$^2$) Individual holes | Area (mm$^2$) Part image |
| --- | --- | --- | --- |
| 1 | Ellipse | 0.7 | 2.8 |
| 2 | Ellipse | 0.3 | 0.3 |
| 3 | Ellipse | 0.5 | 0.5 |
| 4 | Ellipse | 0.5 | 0.5 |
| 5 | Ellipse | 0.4 | 0.4 |
| 6 | Circle | 0.5 | 0.5 |

Plate 3 is shown in FIG. 4, and plate 5 is shown in FIG. 5.

TABLE 2 principal patern

| Plate designation | Form | Area (mm$^2$) Individual holes | Area (mm$^2$) Part image |
| --- | --- | --- | --- |
| 1 | Flower comprising six elements, circle in the middle | 11 | 46 |
| 2 | Five sectors of a circle form a flower | 4 | 20 |
| 3 | Flower comprising six equally large circles | 6 | 36 |
| 4 | Flower comprising six elements, circle in the middle | 7 | 29 |
| 5 | Flower comprising four hearts, circle in the middle | 10 | 45 |
| 6 | Small flower comprising 2 irregular ovals + circle in the middle | 14 | 27 |

TABLE 3

Size relationship between principal pattern and background pattern

| Plate designation | Individual/ individual |
| --- | --- |
| 1 | 16 |
| 2 | 13 |
| 3 | 12 |
| 4 | 14 |
| 5 | 25 |
| 6 | 28 |

TABLE 4

Result for nonwoven material

| Designation, nonwoven material | Plate designation on which nonwoven material has been hydroentangled | Height $h_1$ of protuberances in the first surface structure (μm above $h_0$)* | Height $h_2$ of protuberances in the second surface structure (μm above $h_0$)* | Difference $h_2 - h_1$ |
| --- | --- | --- | --- | --- |
| A | 1 | 351 | 759 | 408 |
| B | 2 | 299 | 474 | 175 |
| C | 3 | 363 | 643 | 280 |
| D | 4 | 542 | 921 | 379 |
| B | 5 | 230 | 435 | 205 |
| F | 6 | 304 | 465 | 161 |

*$h_0$ is the zero level, i.e. the base level of the nonwoven material on the side that has protuberances In the protuberances in the principal structure, the height $h_2$ has been measured on the protuberance that has the lowest height on the profile curve. The height $h_1$ in the background structure is measured on the protuberance that has the highest height. The heights $h_1$ vary from 230 μm to 542 μm, whereas the heights $h_2$ vary from 435 μm to 921 μm.

Figure 8:
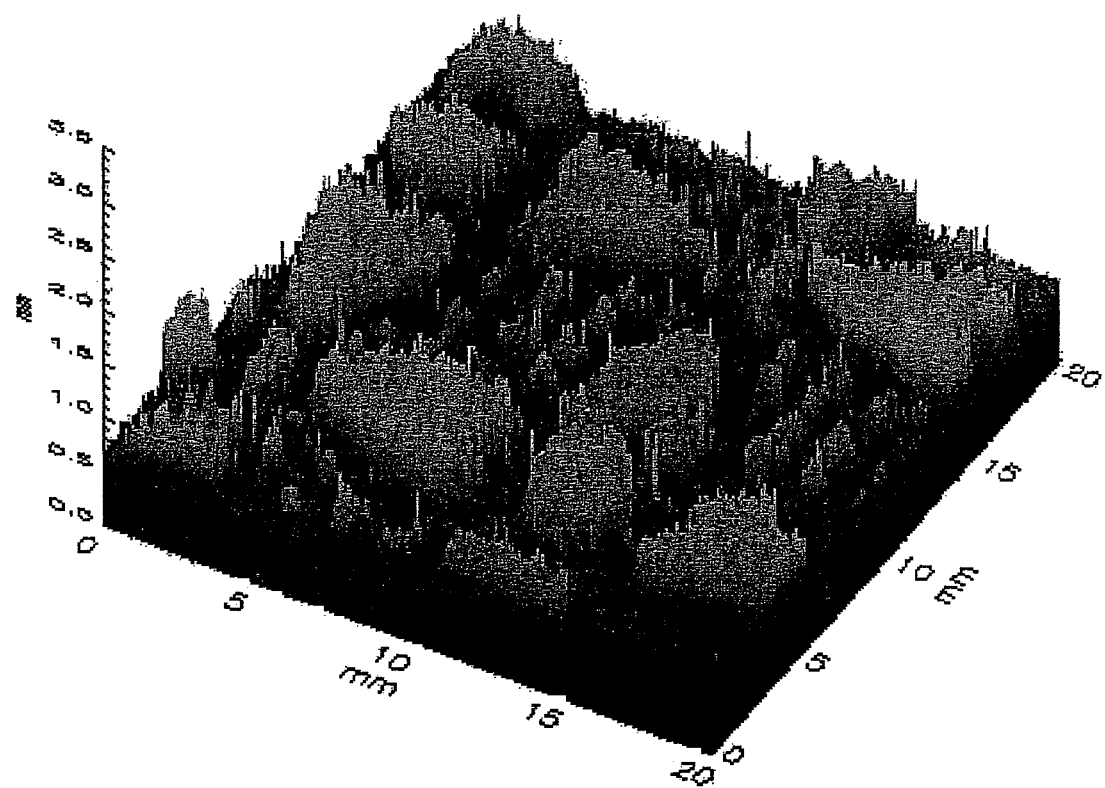
FIG. 8 shows a three-dimensional optical representation of the nonwoven material viewed at an angle from above.

Shown in FIGS. 6 to 8 are the results of the measurements for one of the nonwoven materials. The nonwoven material has been hydroentangled on a plate with the designation 5, as can be seen in FIG. 5. Shown in FIG. 6 is a two-dimensional optical representation of the height measurement for the nonwoven material E, while FIG. 8 shows a three-dimensional optical representation of the nonwoven material E viewed at an angle from above. The surface structure can be seen clearly and corresponds to the pattern that is shown on the plate from FIG. 5. A height profile for the same nonwoven material E is shown in FIG. 7.

Images and decorations have previously been hydroentangled in nonwoven material, although no image has been created in which different surface structures with different heights, $h_1$ and $h_2$ respectively, have been produced, and in which the protuberances in the surface structures occupy areas of different sizes on the base level of the nonwoven material. The nonwoven material in accordance with the invention is moreover essentially smooth on the second side. A strong nonwoven material with a good absorption capacity, the ability to receive fluid and distinct patterns is obtained through the present invention and provides good airiness as a surface material in absorbent products that are produced in accordance with the present invention.

The invention claimed is:

1. An absorbent product comprising:
   a backing layer; and
   a surface layer, the surface layer including a nonwoven material comprising:
      at least one layer of fibres including pulp fibers and at least a fiber selected from amongst synthetic fibres, regenerated fibres and continuous filaments,
      wherein the nonwoven material has a base level $h_0$ with protuberances on a first side, the first side being directed away from the backing layer,
      wherein the protuberances are obtained by hydroentangling and form at least a first and a second surface structure respectively in the form of first and second protuberances from the base level $h_0$,
      wherein the first protuberances have a height $h_1$ from the base level $h_0$ and the second protuberances have a height $h_2$ from the base level $h_0$, where $h_2$ is higher than $h_1$, and each of the second protuberances occupies an area of the surface of the base level at least 4 times greater than an area of the surface of the base level occupied by each of the first protuberances, and wherein there is a difference of at least 100 μm between $h_1$ and $h_2$, and
      wherein the pulp fibres are present in a higher proportion in the protuberances than in the rest of the nonwoven material.

2. The absorbent product as claimed in claim 1, wherein a second side of the nonwoven material is essentially smooth.

3. The absorbent product as claimed in claim 1, wherein each of the second protuberances occupies an area of the surface of the base level at least 8 times greater than an area of the surface of the base level occupied by each of the first protuberances.

4. The absorbent product as claimed in claim 1, wherein the height $h_1$ is at least 200 μm, and the height $h_2$ is at least 300 μm.

5. The absorbent product as claimed in claim 1, wherein there is a difference of at least 200 μm between $h_1$ and $h_2$.

6. The absorbent product as claimed in claim 1, wherein the nonwoven material has additional protuberances with an additional height $h_2^1$ from the base level $h_0$, and wherein the height $h_2^1$ of the additional protuberance is higher than $h_2$ and occupies a larger area of the surface of the base level than the protuberances with the height $h_2$.

7. The absorbent product as claimed in claim 1, wherein the nonwoven material has additional protuberances having at least an additional height $h_1^1$ from the base level $h_0$, and wherein the height $h_1^1$ of the additional protuberance is lower than $h_1$ and occupies a smaller area of the surface of the base level than the protuberances with the height $h_1$.

8. The absorbent product as claimed in claim 1, wherein a total density of the fibres is lower in the protuberances than in the rest of the nonwoven material, calculated in relation to a total quantity of fibres in the protuberances and in the rest of the nonwoven material, respectively.

9. The adsorbent product as claimed in claim 1, comprising an absorbent core between the surface layer and the backing layer.

10. The absorbent product as claimed in claim 9, comprising a transport layer between the surface layer and the absorbent core.

11. The absorbent product as claimed in claim 9, wherein the absorbent core comprises one or more layers of airlaid, fluff pulp, dry defibred or compressed pulp, superabsorbent particles or superabsorbent fibres.

12. The absorbent product as claimed in claim 10, wherein the transport layer comprises one or more of airlaid, wadding, tissue, superabsorbent particles or superabsorbent fibres.

13. The absorbent product as claimed in claim 6, wherein the height $h_1$ is at least 200 μm, and the height $h_2$ is at least 300 μm.

14. The absorbent product as claimed in claim 6, wherein there is a difference of at least 200 μm between $h_1$ and $h_2$.

15. The absorbent product as claimed in claim 6, wherein the nonwoven material has additional protuberances having at least an additional height $h_1^1$ from the base level $h_0$, and wherein the height $h_1^1$ of the additional protuberance is lower than $h_1$ and occupies a smaller area of the surface of the base level than the protuberances with the height $h_1$.

16. The absorbent product as claimed in claim 15, wherein the height $h_1$ is at least 200 μm, and the height $h_2$ is at least 300 μm.

* * * * *